US011581095B2

(12) United States Patent
Helmer (10) Patent No.: US 11,581,095 B2
(45) Date of Patent: Feb. 14, 2023

(54) MEDICAL QUERY ANSWERING APPARATUS

(71) Applicant: SANOFI, Paris (FR)

(72) Inventor: Michael Helmer, Frankfurt am Main (DE)

(73) Assignee: Sanofi, Paris (FR)

(*) Notice: Subject to any disclaimer, the term of this patent is extended or adjusted under 35 U.S.C. 154(b) by 336 days.

(21) Appl. No.: 16/651,437

(22) PCT Filed: Oct. 9, 2018

(86) PCT No.: PCT/EP2018/077431
§ 371 (c)(1),
(2) Date: Mar. 27, 2020

(87) PCT Pub. No.: WO2019/072820
PCT Pub. Date: Apr. 18, 2019

(65) Prior Publication Data
US 2020/0286628 A1 Sep. 10, 2020

(30) Foreign Application Priority Data

Oct. 10, 2017 (EP) .................................. 17306364

(51) Int. Cl.
*G06F 16/90* (2019.01)
*G16H 50/70* (2018.01)
(Continued)

(52) U.S. Cl.
CPC ............ *G16H 50/70* (2018.01); *G06F 3/167* (2013.01); *G06F 11/3476* (2013.01); *G06F 16/90335* (2019.01); *G16H 40/67* (2018.01)

(58) Field of Classification Search
None
See application file for complete search history.

(56) References Cited

U.S. PATENT DOCUMENTS

| 7,640,264 B1* | 12/2009 | Chaulk | G06F 16/2428 |
| | | | 707/999.005 |
| 2005/0089150 A1* | 4/2005 | Birkhead | H04M 3/4938 |
| | | | 379/88.14 |

(Continued)

FOREIGN PATENT DOCUMENTS

| EP | 3010015 | 4/2016 |
| JP | 2003-006316 | 1/2003 |

(Continued)

OTHER PUBLICATIONS macadamian.com [online], Didier Thizy, "Using Amazon Alexa voice service in healthcare macadamian", Macadamian Technologies, Jun. 29, 2016, Retrieved from the Internet: URL <www.macadamian.com/2016/06/29/amazons-alexa-voice-service-in-healthcare>, 9 pages.

(Continued)

*Primary Examiner* — Craig C Dorais
(74) *Attorney, Agent, or Firm* — Fish & Richardson P.C.

(57) ABSTRACT

The application relates to providing medical information in response to a query, in particular, although not exclusively, to a method of querying a medical database using voice recognition. According to an embodiment, there is provided a medical query answering apparatus that is configured to convert detected audio signals into a natural language data stream; determine from the natural language data stream whether a voice command for information relating to a medical device or a medicament has been issued by a user; in response to a positive determination, convert at least part of the natural language data stream into a query for querying a medical database; supply the query to the medical database and receive a response therefrom; and provide an audio output based at least in part on the response from the medical database.

18 Claims, 3 Drawing Sheets

(51) Int. Cl.
  *G16H 40/67*     (2018.01)
  *G06F 16/903*    (2019.01)
  *G06F 3/16*      (2006.01)
  *G06F 11/34*     (2006.01)

(56) References Cited

U.S. PATENT DOCUMENTS

| | | | |
|---|---|---|---|
| 2014/0032223 A1 | 1/2014 | Powe | |
| 2016/0071432 A1* | 3/2016 | Kurowski | G16H 20/30 |
| | | | 434/236 |
| 2017/0162197 A1* | 6/2017 | Cohen | G10L 15/22 |
| 2018/0025127 A1* | 1/2018 | Bagchi | G06F 16/31 |
| | | | 705/2 |

FOREIGN PATENT DOCUMENTS

| | | |
|---|---|---|
| JP | 2011-150682 | 8/2011 |
| JP | 2015-191558 | 11/2015 |

OTHER PUBLICATIONS

PCT International Preliminary Report on Patentability in Application No. PCT/EP2018/077431, dated Apr. 14, 2020, 9 pages.
PCT International Search Report and Written Opinion in Application No. PCT/EP2018/077431, dated Jan. 14, 2019, 11 pages.

* cited by examiner

MEDICAL QUERY ANSWERING APPARATUS

CROSS REFERENCE TO RELATED APPLICATIONS

The present application is the national stage entry of International Patent Application No. PCT/EP2018/077431, filed on Oct. 9, 2018, and claims priority to Application No. EP 17306364.5, filed on Oct. 10, 2017, the disclosures of which are incorporated herein by reference.

TECHNICAL FIELD

The application relates to providing medical information in response to a query, in particular, although not exclusively, to a method of querying a medical database using voice recognition.

BACKGROUND

A Patient Information Leaflet (PIL) or Package Insert is often provided with licensed medicines in order to inform medicine users of how to take the medicine, potential side effects of the medicine and interactions the medicine may have with other medication or pre-existing medical conditions, as well as provide any other information deemed useful for the user.

SUMMARY

According to an aspect hereof, there is provided a method of providing medical information comprising: converting detected audio signals into a natural language data stream; determining from the natural language data stream whether a voice command for information relating to a medical device or a medicament has been issued by a user; in response to a positive determination, converting at least part of the natural language data stream into a query for querying a medical database; supplying the query to the medical database and receiving a response therefrom; and providing an audio output based at least in part on the response from the medical database. This allows a user to request and be provided with information relating to their medication or medical devices.

The method may further comprise transmitting the query to a data server comprising the medical database, the data server being remotely located from the user. This allows a large medical database to be queried to determine a response. It also allows for the medical database to be kept up to date without the user having to download updates.

The method may further comprise determining if a suitable response to the query is present in the medical database; and in the event of a negative determination, transmitting the query to a secondary query answering facility. Transmitting the query to a secondary query answering facility may allow queries that do not have answers in the medical database to be responded to. The method may comprise receiving a new response from the secondary query answering facility; and providing an audio output based at least in part on the new response from the secondary query answering facility. This allows queries that do not have answers in the medical database to be responded to.

Optionally, the new response is generated at the secondary query answering facility in a text format and the audio output is created from the new response using a text-to-speech process.

The method may further comprise: transmitting the new response to the medical database; and storing the new response in the medical database together with metadata relating to the query. This is a straightforward method of providing a response from the secondary medical answering.

The response may comprise video data and the method further comprise: transmitting the response to a display device; and providing a video output on the display device based at least in part on the video data in the response. Providing video data as part of the response can allow more detailed answers to a query to be provided, particularly when providing instructions for how to use a medical device or medicament.

The method may further comprise: determining a user identity; retrieving user data from a user database using the user identity; and modifying the audio output based at least in part in the user data. This allows the query response to be tailored to the user supplying the query. In particular, it can allow the user to be informed of interactions between medicaments that the user is taking.

For increased security, the method may further comprise verifying the user identity prior to retrieving the user data from the user database.

The method may further comprise: creating a log of the query, the log comprising the user identity, an identifier of the query and an identifier of the response provided; and storing the log in the medical database. This can provide a record of what information has been supplied to a particular user.

The determining of whether the voice command has been issued by a user may comprise: identifying one or more potential voice commands in the natural language data stream; calculating a confidence level for each of the identified potential voice commands; selecting a potential voice command based on the calculated confidence levels; comparing the confidence level of the selected voice command to a pre-defined threshold confidence level; and where the confidence level of the selected voice command is above the pre-defined threshold confidence, making a positive determination that the selected voice command is present. The use of confidence levels in determining whether a voice command is present can assist in preventing a query being incorrectly identified.

The method may further comprise providing a request for a user to repeat a voice command where a positive determination that more than one selected voice command is present has been made. This can prevent incorrect information being supplied in response to a query.

The query may be selected from a list of pre-determined permissible queries. This can lead to more accurate query determination.

According to an aspect of the present disclosure, there is provided an apparatus comprising a processor; and a memory, including computer program code which, when executed by the at least one processor, causes the apparatus to perform the method of any of the aspects described above.

According to an aspect of the present disclosure, there is provided a system for performing the method of any of the aspects described above, the system comprising: a speaker; a microphone; a processor arrangement; and a medical database.

These and other aspects will be apparent from and elucidated with reference to the embodiments described hereinafter.

BRIEF DESCRIPTION OF THE DRAWINGS

Embodiments will now be described, by way of example only, with reference to the accompanying drawings, in which:

FIG. 4 is an overview showing further functionality of an interactive medical query system.

DETAILED DESCRIPTION

Embodiments provide a system and method for answering user queries relating to medical information, particularly those relating to medication and/or medical devices.

Figure 1:
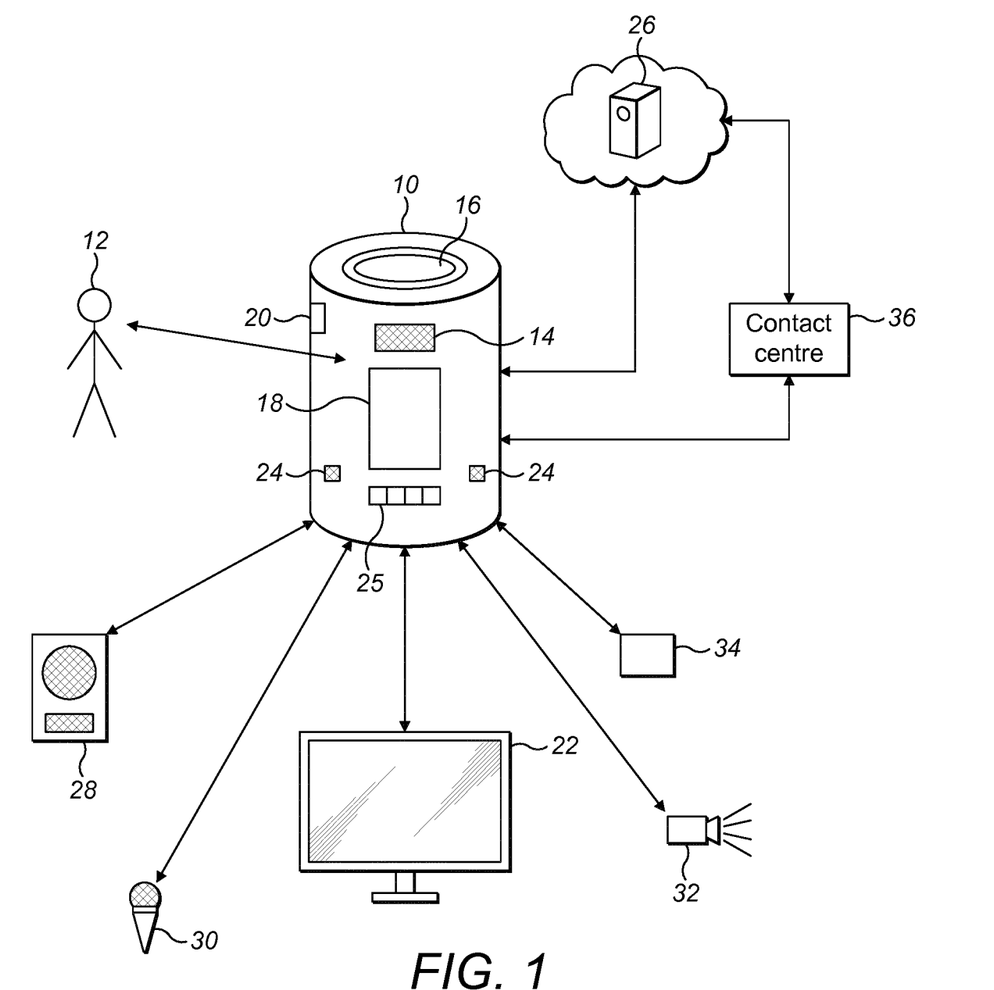
FIG. 1 is an overview of an interactive medical query system according to a first embodiment.

With respect to FIG. 1, an overview of an interactive medical query system according to a first embodiment is shown. With respect to FIG. 2, a schematic representation of the electronics system of the apparatus according to the first embodiment is shown. A medical query answering apparatus 10, in the example shown in the form of a "smart speaker", is provided with which a user can interact using voice commands.

If a medication user 12 fails to fully read the PIL, it may leave the medication user 12 lacking information about the medicine or unsure as to how to correctly administer it. Furthermore, even if the user does fully read the PIL, he or she may have further queries regarding the medication. Verification that a user was informed about the PIL content would also be useful for the manufacturer.

Also, instructions for medical devices may not be completely read by a user 12, which can result in user errors when the device is being used. Even if fully read, the user may also have further queries regarding the device, for example regarding troubleshooting.

Figure 2:
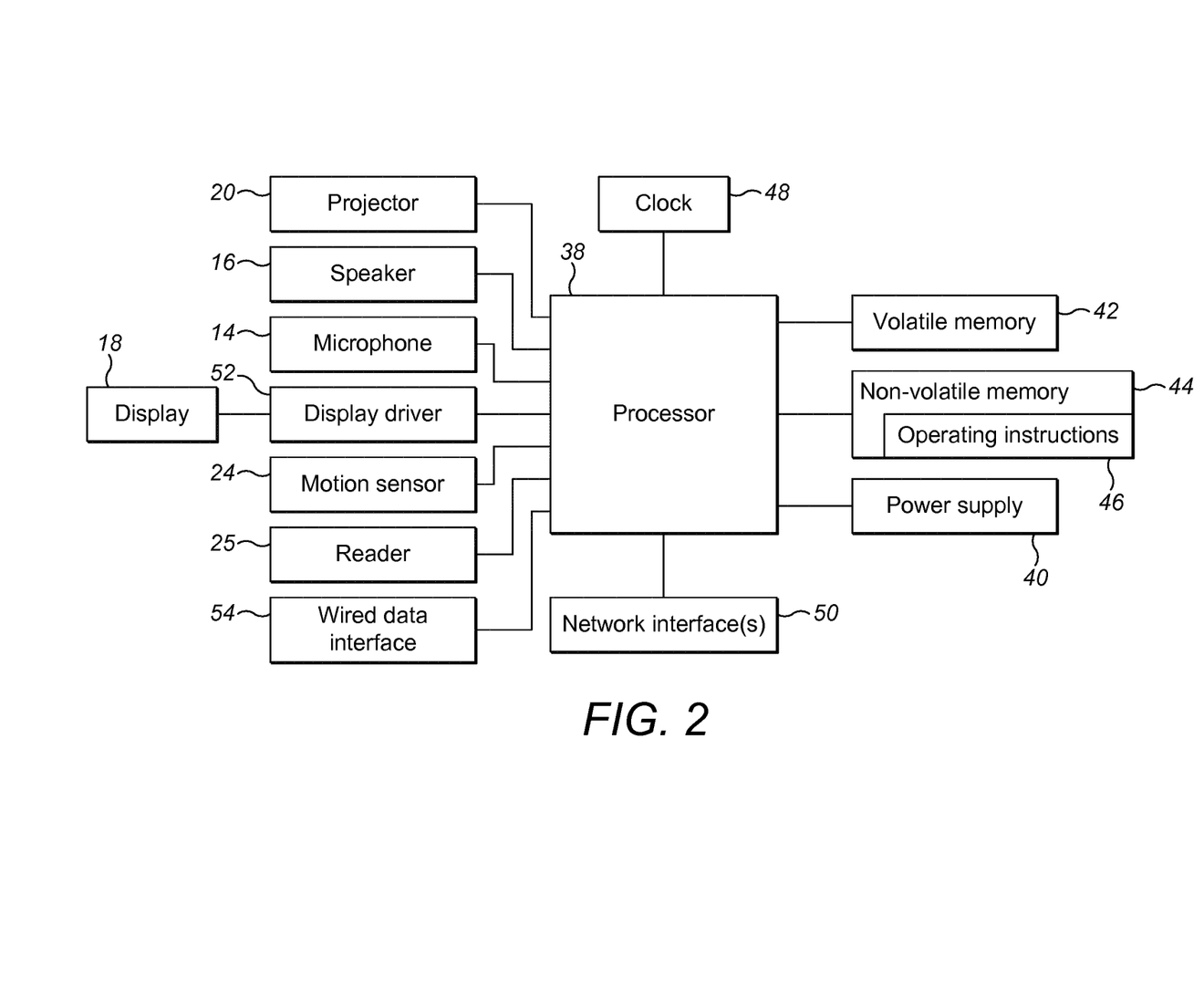
FIG. 2 is a schematic representation of the electronics system of the medical query answering apparatus of the system according to the first embodiment.

The apparatus 10 comprises a microphone 14 for receiving audio signals. The microphone 14 comprises a transducer for converting sound into electronic audio signals, which can then be processed.

The apparatus also comprises a processor arrangement 38 configured to perform voice recognition on audio signals received by the microphone 14. When audio signals are received by the microphone 14, the processor arrangement 38 can convert the audio signals into a natural language stream and then further process the natural language stream to determine whether a voice command is present in the audio signal. Said voice command may comprise a pre-defined command, such as an activation command for the device or a predefined query, or a question regarding a medication, application of a medication, a medical device, a personal medication history or a due date.

The apparatus further comprises a speaker 14 for transmitting audio signals to the user 12 in the form of sound. The speaker 14 orientation can support a spatial natural sound rendering.

A network interface 50 is also provided on the apparatus in order to connect apparatus to a network. The network interface 50 may be provided, for example, by one or more of: a Wi-Fi interface; an Ethernet interface; a Bluetooth transceiver; and/or a USB interface. The apparatus 10 can connect to a local area network (LAN) and/or the Internet via the network interface 50, allowing it to exchange data with other members of the network. The apparatus may also use the network interface to connect directly with additional devices, using, for example, a Bluetooth connection.

The apparatus may comprise a display 18. Optionally the display 18 has with touch screen capability. The display 18 can provide a visual indication of the status of the apparatus, such as a mode the apparatus is in, a battery status, and/or whether a power supply is connected. The display 18 can also be used to communicate messages to the user. The display 18 can be in the form of a Liquid Crystal Display (LCD), Light Emitting Diode (LED), or Organic Light Emitting Diode (OLED) screen or similar.

The apparatus may also comprise a projector 20 to project information and/or instructions to the user, for example new messages may be projected onto a wall near the apparatus. The apparatus may therefore contain an adjustable Projector 20, in some embodiments in the form of an LED projector. In some embodiments, the projector 20 can replace an external display device 22 for display of video clips providing instructions or information.

In some embodiments, the display 18 may include touch screen functionality, allowing the display 18 to receive user inputs. The touch screen functionality can be used to support installation and troubleshooting procedures. Alternatively or additionally, the display 18 may be accompanied by one or more push buttons or keys in the vicinity of the display, allowing the user to interact with the apparatus, for example by navigating a cursor through a collection of menus and options on the display 18. A remote control may also be provided for interacting with the apparatus.

The apparatus may comprise a motion sensor 24. The motion sensor 24 can be provided in the form of an infra-red sensor, an ultrasound sensor, or can be integrated with the microphone 14. The motion sensor 24 can allow the device to react when motion is detected nearby, such as motion of a user 12 in the room where the apparatus is located, for example by "waking up" from a stand-by mode and starting to listen for voice commands. Additionally, detection of motion by the motion sensor 24 may be used as a trigger for the apparatus to provide a spoken reminder to a user relating to medication. Such reminders may include a reminder that a dose of medication is due to be taken.

The apparatus 10 may, in some embodiments, comprise an RFID reader 25, or more generally a near field communications transceiver. RFID tags may then be read by the apparatus 10. The reader 25 may alternatively or additionally include a QR-code reader, bar-code reader, or other optical code reader. The reader 25 may allow for the registration of medications that the user is using. This can provide information relating to the user's stock of medication, such as the amount of medication the user has been provided with or batch numbers of the medication.

The apparatus can be provided in many forms, including, but not limited to: a smart speaker; a mobile device, such as a smart phone or tablet running an application; a laptop; or a personal computer. In some embodiments it can be provided as a collection of separate components distributed throughout a location and/or integrated with other user devices in a location.

The apparatus is connected to a data server[1] 26 comprising a medical database via the network interface 50. Through this connection the apparatus can share data in a bi-directional manner with the data server 26. The data server 26 can be remotely located from the apparatus 10, for example at a data centre controlled by a medicine supplier or a device manufacturer. Alternatively, the data centre 26 can be part of a distributed computer system, such as "the cloud". In some embodiments, the data server 26 may be located locally to the apparatus on the same Local Area Network.

The medical database contains pre-defined responses to medical queries, such as those relating to medication and/or medical devices. In some embodiments, it may also contain personal medical details relating to one or more users of the system, for example a list of medication currently being taken by the user and any past or present medical conditions. This can allow responses to user queries to be tailored to the particular user to whom the query relates.

In some embodiments, the network interface can further be used to connect to additional devices on the same Local Area Network as the apparatus. Examples of additional devices include display devices 22, such as a television or tablet PC, additional speakers 28 and microphones 30, and/or a projector 32, or medical devices 34.

The network interface may, in some embodiments, comprise a telephone interface. This can allow the apparatus 10 to dial an emergency number or hotline upon a voice request from the user 12. In some embodiments, data from medical devices 34 connected to the apparatus via the network interface 50 can act as a trigger for calling the emergency number or hotline. For example, if a medical device reading, such as a blood glucose level, is detected to be critical, the apparatus 10 may request a response form the user 12. In the absence of a response, the apparatus 10 can automatically dial the hotline to request assistance for the user 12.

The data server 26 is further supported by a secondary query answering facility 36, such as a contact centre, connected to the network comprising both the data server 26 and the apparatus 10. The secondary query answering facility 36 can communicate with both the data server 26 and the apparatus 10. The secondary query answering facility 36 can be manned by a human Agent, who can manually add additional query responses to the medical database when no suitable response to the query has been found, and who can additionally transmit the new response to the apparatus 10.

As best seen in FIG. 2, the electronics system comprises the processor arrangement 38. The processor arrangement 38 and other hardware components may be connected via a system bus (not shown). Each hardware component may be connected to the system bus either directly or via an interface. A power supply 40 is arranged to provide power to the electronics system. In some embodiments a battery may also be provided to enable the use of the apparatus without a power connection to the mains supply. Said battery may be rechargeable.

The processor arrangement 38 controls operation of the other hardware components of the electronics system. The processor arrangement 38 may be an integrated circuit of any kind. The processor arrangement 38 may for instance be a general purpose processor. It may be a single core device or a multiple core device. The processor arrangement 38 may be a central processing unit (CPU) or a general processing unit (GPU). Alternatively, it may be a more specialist unit, for instance a RISC processor or programmable hardware with embedded firmware. Multiple processors may be included. The processor arrangement 38 may be termed processing means.

The electronics system comprises a working or volatile memory 42. The processor arrangement 38 may access the volatile memory 42 in order to process data and may control the storage of data in memory. The volatile memory 42 may be a RAM of any type, for example Static RAM (SRAM), Dynamic RAM (DRAM), or it may be Flash memory, such as an SD-Card. Multiple volatile memories may be included, but are omitted from the Figure.

The electronics system comprises a non-volatile memory 44. The non-volatile memory 44 stores a set of operation instructions 46 for controlling the normal operation of the processor arrangement 38. The non-volatile memory 44 may be a memory of any kind such as a Read Only Memory (ROM), a Flash memory or a magnetic drive memory. Other non-volatile memories may be included, but are omitted from the Figure.

The processor arrangement 38 operates under the control of the operating instructions 46. The operating instructions 46 may comprise code (i.e. drivers) relating to the hardware components of the electronics system, as well as code relating to the basic operation of the apparatus. The operating instructions 46 may also cause activation of one or more software modules stored in the non-volatile memory 44. Generally speaking, the processor arrangement 38 executes one or more instructions of the operating instructions 36, which are stored permanently or semi-permanently in the non-volatile memory 44, using the volatile memory 42 temporarily to store data generated during execution of the operating instructions 46.

The processor arrangement 38, the volatile memory 42 and the non-volatile memory 44 may be provided as separate integrated circuit chips connected by an off-chip bus, or they may be provided on a single integrated circuit chip. The processor arrangement 38, the volatile memory 42 and the non-volatile memory 44 may be provided as a microcontroller.

The electronics system comprises a clock 48. The clock 48 may be a clock crystal, for example, a quartz crystal oscillator. The clock 48 may be a separate component to the processor arrangement 38 which is configured to provide a clock signal to the processor arrangement. The processor arrangement may be configured to provide a real time clock based on the signal from the clock 48. Alternatively, the clock 48 may be a clock crystal which is provide on a single integrated circuit chip with the processor arrangement 38. Other possibilities include a radio controlled clock or time adjustment by internet connection.

The electronics system comprises one or more network interfaces 50. The network interfaces 50 facilitate the connection of the apparatus to one or more computer networks and the bi-directional exchange of information between the apparatus and other members of the networks.

These networks may include the Internet, a Local Area Network, or any other network required by the apparatus to communicate with the data centre and/or contact centre. The network interfaces 50 comprise a network interface controller, such as an Ethernet adaptor, a Wi-Fi adaptor and/or a Bluetooth adaptor. The network interfaces 50 are associated with one or more network addresses for identifying the apparatus on the network. The one or more network addresses may be in the form of an IP address, a MAC address, and/or an IPX address.

The electronic system comprises a microphone 14. The microphone 14 can be operated to receive an input in the form of a sound, and to convert said sound into an electronic audio signal capable of being processed in the digital domain.

The processor arrangement 38 is configured to convert any audio signal detected by the microphone 14 into a natural language data stream. The processor arrangement 38 may implement a speech-to-text algorithm in order to convert the audio signal into a natural language stream. Such algorithms can include Hidden Markov Models, Dynamic Time Warping, or Neural Networks. The processor arrangement 38 is further configured to analyse the natural language data stream in order to determine if a voice command is present in the natural language data stream. The processing arrangement 38 can achieve this by identifying potential voice commands in the natural language data stream and assigning to each of the potential voice commands a confidence level.

The processor arrangement 38 is further configured to create an audio output based at least in part on a response received by the apparatus from the medical database 26. This can involve decoding or uncompressing the response.

The electronics system also comprises a speaker 16. The speaker is an example of an audio transducer. The speaker 16 can be operated to provide an audio output in the form of spoken word, or more generally any sound. The processor arrangement 38 operates the speaker 16 to provide an audio output based on responses received from the medical database 26 and/or on conditions present in the operating instructions 46 of the processing arrangement.

The electronics system may comprise a display driver 52. The display driver 52 may be provided as a separate integrated circuit chip to the processor arrangement 38, which is connected by an off-chip bus. Alternatively, the display driver 52 may be provided on a single integrated circuit chip with the processor arrangement 38.

The electronics system may comprise a display 18 of the user interface. The display 18 can be operated by the processing arrangement 38 via the display driver to provide one or more visual notifications to a user. The display 18 can provide a visual indication of the status of the apparatus, such as which mode the apparatus is in, a battery status, and/or whether a power supply is connected. In some embodiments, the display 18 is in the form of a touch screen display.

The processor arrangement 38 may check the state of charge of one or more batteries (not shown) included in the packaging assembly. If the state of charge is determined to be low, the display may be operated to show a battery low warning.

The electronics system may further comprise a motion sensor 24. The motion sensor 24 can be a dedicated motion sensing device, such as an infra-red detector or ultrasound detector, or may be integrated with the microphone. The motion sensor 24 is monitored by the processing arrangement 38 for a signal indicating that motion has been detected. Such a signal can be used to wake the apparatus up from a standby mode and put the apparatus into a listening state. The signal can also act as a trigger for the processing arrangement to control the speaker 16 to output a reminder to a user 12, such as a reminder that the user is due to take a dose of medicine.

In some embodiments, the processor arrangement 38 in the apparatus may not be sufficiently powerful to perform one or more of the functions described above. Instead, the processing arrangement 38 is configured to communicate via the network interface 50 with an additional computer system that has more computing power available to it. The processor arrangement 38 can transmit data from the apparatus to the additional computer system, where it can be processed using the additional computing power of the additional computer system. The additional computer system can return the results of this processing back to the processor arrangement 38 for further processing. The additional computing system can, for example, be a remote computer system, a distributed computer system, or part of a data centre.

The electronics system may comprise a wired (non-wireless) data interface 54. The wired data interface 54 provides a means for wired connectivity with external devices. The external devices may include, for example, a medical device or a personal computer, such as a laptop computer, desktop computer, tablet computer etc. In some embodiments, a battery in the apparatus 10 can be charged via the data interface 54. The wired data interface 54 may be in the form of a Universal Serial Bus (USB) port, for instance a micro-USB or USB-C port.

Figure 3:
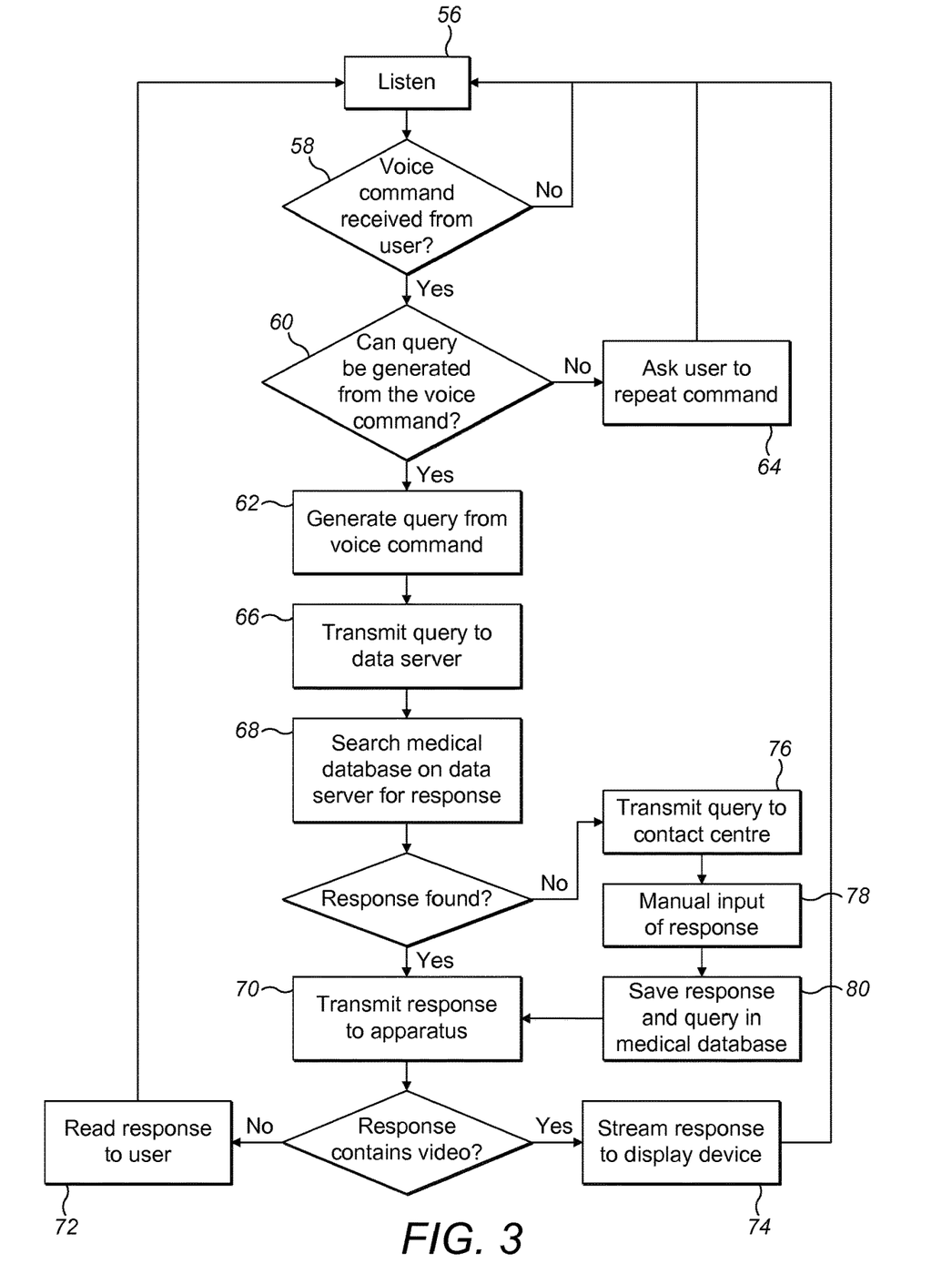
FIG. 3 is a flow diagram of a method of providing medical information in response to a query.

With respect to FIG. 3, a flow diagram of a method of providing medical information according to an embodiment is shown. The method is performed by a medical query system, for example the system described in relation to FIG. 1. In its default state, referred to as the listening state 56, the apparatus 10 monitors audio signals input via one or more microphones 14 present in the system, listening for any potential voice commands. In some embodiments, the default state can instead be a standby state where the apparatus 10 is not actively listening for voice commands and is in a low power mode, with the listening state 56 only activated upon detection of a trigger, such as if motion is detected near a microphone in the system by a motion sensor 24.

Audio signals input into the system via a microphone 14 are converted into a natural language data stream using, for example, a speech-to-text algorithm. The natural language data stream is then analysed to determine if the input audio signals comprise a voice command 58 from a user 12. Potential voice commands in the audio stream are identified and are each assigned a confidence score. The confidence score can, for example, be based on how closely the potential voice command matches a pre-determined voice command. The confidence score is used to select one or more of the potential voice commands for further analysis. If the confidence level of the one or more selected voice commands being present is above some threshold confidence level, then that voice command is identified in the audio stream. Typically, the voice command with the highest confidence score that is above the threshold confidence level is determined to be the voice command present in the natural language data stream. However, where multiple voice commands are identified in the audio stream with similar confidence scores that are above the threshold, the system can instruct the user to repeat the voice command via a speaker in the vicinity of the user. The system then returns to the listening state.

If no voice command is determined to be present, the system returns to the listening state 56.

If a voice command is determined to be present in the natural language stream, the system attempts to convert at least a part of the natural language stream into a query 60 for a medical database 26. A confidence level for the query generated in this way may also be determined. For example, the query could be selected from a pre-defined list of permissible queries, with the confidence level determined from how closely the natural language stream matches the pre-defined query. In this way, the system generates a query form the voice command 62.

If this confidence level falls below a pre-determined threshold confidence, then the system instructs the user 12 via a speaker in the vicinity of the microphone 14 into which the audio signals were input to repeat the command 64. The system then returns to the listening state 56.

If the confidence level is above the pre-determined threshold confidence, then the generated query is transmitted 66 to a data server 26. The data server 26 uses the generated query to query a medical database 68 to determine a response to the voice command input by the user 12. If a response to the query is present in the database, the response is transmitted 70 back to the part of the system local to the user, such as the medical query answering apparatus 10 described in relation to FIGS. 1 and 2.

The system uses the determined response to provide an audio output 72 that can be communicated to the user 12 via a speaker 16 in the system. The audio output 72 is determined at least in part from the response to the query received from the medical database, and optionally also from additional user information stored in the system. Such additional information may, for example, include information relating to a user identity, a user medical history or a user medication regime. In some embodiments, the audio output 72 is generated from the response using a text-to-speech algorithm.

In some embodiments, the response may contain video data. If video data is present in the response, the user may be provided with the option to stream the video data 74, or a part of it, to a display device capable of video playback that is connected to the system. The display device may also provide an audio output associated with the video that is derived from the response. Providing a video stream to a display device can be particularly useful when the query relates to the use of a medical device, or when the user is using a medical device for the first time. In embodiments where a display is provided on the medical query answering apparatus, the video data may be presented on the apparatus display. In embodiments where the apparatus comprises a LED projector, the video data may be projected onto a wall or screen near the apparatus.

If a response to the query is not found in the medical database[2], the system can transmit the query 76 to a secondary query answering facility 36, such as a contact centre. The transmission can occur, for example, by automatically creating an email containing the query at the medical database, and then sending the email to the contact centre. At the contact centre a contact centre agent can read the query and manually input a new response 78 to the query into the system. Typically, this newly generated response will be input by the agent in a text format via a keyboard, though may alternatively be input by voice.

The newly generated response to the query can be transmitted to the medical database, where it can be stored along with the query for future reference 80. The response may be stored together with metadata relating to the request, such as the confidence level of the query, the time and/or date of the query, the time and/or date that the new response was created, the identity of the call centre agent who created the response, and/or the medication or medical device that the request related to. In some embodiments, the metadata may contain the geographic location that the response relates to, for example to allow for the response to be tailored to any regulations in force at the user's location. The metadata can allow the response to be identified when similar queries are provided by users in the future.

The newly generated response may be modified before storage in the medical database. This modification may comprise, for example, altering the format of the response, compression of the response for more efficient storage and/or the addition of metadata to the response. Modification of the newly generated response may occur at the data server 26. Modification of the newly generated response may alternatively or additionally occur at the contact centre, for example as part of a quality control or verification process. The stored responses can also be accessed for modification after they have been stored in the medical database, for example to correct errors or update the responses with new information.

The newly generated response is then transmitted 70 to the part of the system local to the user 12 as described above, as if it had always been present in the database, and communicated to the user 12.

In some embodiments the option exists for the contact centre agent to initiate an audio link with the user 12 via the system. The user 12 and contact centre agent can then communicate verbally to resolve the query. Use of this feature can allow queries that are particularly complicated or ambiguous to be answered, as well as providing the opportunity for the user 12 to provide additional information and/or context relating to the query.

In all cases, a log of the query and the response can be stored in the medical database, along with metadata relating to the query, such as the identity of the user 12 and/or time of the query. This can provide evidence that a user 12 has been provided with a particular piece of information from the PIL.

In some embodiments, the audio input can be used to identify the user 12 issuing the voice command. Speaker recognition algorithms can be used to determine the identity of the user 12 from characteristics of the user's voice that are input into the system as part of the audio stream. Alternatively, the user 12 can identify themselves and verify their identity through an interface with the system, such as a touch screen display, for example using a user name and password.

Identifying the user inputting the voice commands allows the response to the query to be tailored to the identified user 12 using previously stored information about that user 12. For example, medical records of the user 12 can be used to determine if additional information or warnings need to be included in the response, such as whether the medication the user is querying has an interaction with any other medication that the user is taking or any conditions the user may have. The medical records may also comprise a timetable of when the user is scheduled to take doses of medication, which can be used to issue reminders to the user to take the medication at the required time.

If, for example, an identified user 12 queries information regarding the dosage of a medication, the system checks the identified user's medication regime, as stored in a database or other memory, to discover what the user's dosage for that medicine should be. This dosage is then be used to determine a response to the user's query that includes the required dosage of the queried medication for that user. If the system finds the medication the user is inquiring about is not part of the user's medication regime, the response to the user's query may include a warning that the user is not required to take that medication.

Furthermore, the system may check the user's medical records or medication regime and find that the medication the user is enquiring about has adverse reactions or conflicts with one or more other medications in the user medication regime and/or medical conditions that the user has. In this situation, the response to the query can include a warning to the user not to take the medication they are inquiring about. In some embodiments, it may also include in the response instructions for what the user should do if the user has taken the conflicting medication, for example an instruction to contact the user's doctor immediately.

The system may, in some embodiments, also use the user identity to issue reminders to the user 12. If a user 12 is identified, the response to the user's query can include a reminder to, for example, take a medication. The system can look up the user's medication timetable and compare the scheduled time for the user to take a medication with the current time. If the current time is within a predefined window of the scheduled time for the user 12 to take a medication, then the response to the user query can additionally contain a reminder to the user 12 that they should prepare to take or should have taken the scheduled medication. The reminder can alternatively or additionally be given when the user 12 is identified without the user 12 having to provide a query to the system.

The system may, in some embodiments, provide the user 12 with news or updates relating to a medication or medical device in response to a user 12 requesting if any news is available. For example, if a user 12 requests "new messages", the system may provide news about the medication or medical device via the speaker or display device. The news or updates may be provided by the medication manufacturer, regulators, medication agencies and/or defined newsletter forums.

In some embodiments, the system may read email messages to a user 12 that have been provided by a medical practitioner, such as a doctor or a manufacturer, that relate to the administration or dosage of a medication.

In some embodiments, the user medical records may be accessed by an authorised third party, such as a medical practitioner/doctor. The third party may update the user medical records. The updated user records can then be used to respond to queries from the user 12. For example, a doctor can define the correct dosage for a medication into a user's records, which can then be used to answer queries by that user relating to the user dosage regime. In some embodiments, updated user information can be communicated to the user upon the presence of that user being identified.

Providing the system access to a user's medical records can require further verification of the user identity due to the sensitivity and privacy of the records. The user's identity can be verified by requiring the user to input a password when a query is raised that requires access to the user's medical record. The password can be spoken by the user to the system via a microphone. Alternatively or additionally, it could be input by the user by hand into the device using a touchscreen display, a set of keys, or a remote control.

In some embodiments, the reader 25 can be used to register user medication. When a first use of a medication by a user 12 is detected, the apparatus can read the PIL and/or Instructions for Use to the user. The instructions can be read in the native language of the user 12, as determined from the user records. This can provide a verified indicator that the user 12 has been informed of the PIL.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same subject matter as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of this disclosure, the scope of which is defined in the claims.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A method of providing medical information, the method comprising:
    converting detected audio signals into a natural language data stream;
    determining from the natural language data stream whether a voice command for information relating to a medical device or a medicament has been issued by a user;
    in response to a positive determination, converting at least part of the natural language data stream into a query for querying a medical database;
    supplying the query to the medical database and receiving a response therefrom;
    generating an audio output based at least in part on the response from the medical database;
    determining a user identity of the user;
    retrieving user data from a user database using the user identity;
    modifying the audio output based at least in part on the user data;
    providing the audio output;
    creating a log of the query, the log comprising the user identity, an identifier of the query, and an identifier of the response provided; and
    storing the log in the medical database.

2. The method of claim 1, further comprising transmitting the query to a data server comprising the medical database, the data server being remotely located from the user.

3. The method of claim 1, further comprising:
    determining if a suitable response to the query is present in the medical database;
    making a negative determination;
    in response to making the negative determination, transmitting the query to a secondary query answering facility.

4. The method of claim 3, further comprising:
    receiving a new response from the secondary query answering facility; and
    providing an audio output based at least in part on the new response from the secondary query answering facility.

5. The method of claim 4, wherein the new response is generated at the secondary query answering facility in a text format and the audio output is created from the new response using a text-to-speech process.

6. The method of claim 4, further comprising:
    transmitting the new response to the medical database; and
    storing the new response in the medical database together with metadata relating to the query.

7. The method of claim 1, wherein the response comprises video data, and wherein the method further comprises:
    transmitting the response to a display device; and
    providing a video output on the display device based at least in part on the video data in the response.

8. The method of claim 1, further comprising verifying the user identity prior to retrieving the user data from the user database.

9. The method of claim 1, wherein determining whether the voice command has been issued by a user comprises:
    identifying one or more potential voice commands in the natural language data stream;

calculating one or more confidence levels respectively for the one or more potential voice commands;

selecting a potential voice command of the one or more potential voice commands based on the one or more confidence levels;

comparing a confidence level of the potential voice command that is selected to a pre-defined threshold confidence level; and where the confidence level of the potential voice command that is selected is above the pre-defined threshold confidence, making a positive determination that the potential voice command that is selected is present.

10. The method of claim 9, further comprising providing a request for a user to repeat a voice command where a positive determination that more than one selected voice command is present has been made.

11. The method of claim 1, wherein the query is selected from a list of predetermined permissible queries.

12. An apparatus for providing medical information, the apparatus comprising:

a processor; and a memory including computer program code which, when executed by the processor, causes the apparatus to perform operations comprising:

converting detected audio signals into a natural language data stream;

determining from the natural language data stream whether a voice command for information relating to a medical device or a medicament has been issued by a user;

in response to a positive determination, converting at least part of the natural language data stream into a query for querying a medical database;

supplying the query to the medical database and receiving a response therefrom;

generating an audio output based at least in part on the response from the medical database;

determining a user identity of the user;

retrieving user data from a user database using the user identity;

modifying the audio output based at least in part on the user data;

providing the audio output;

creating a log of the query, the log comprising the user identity, an identifier of the query, and an identifier of the response provided; and storing the log in the medical database.

13. The apparatus of claim 12, wherein the operations further comprise transmitting the query to a data server comprising the medical database, the data server being remotely located from the user.

14. The apparatus of claim 12, wherein the operations further comprise:

determining if a suitable response to the query is present in the medical database;

making a negative determination;

in response to making the negative determination, transmitting the query to a secondary query answering facility.

15. The apparatus of claim 14, wherein the operations further comprise:

receiving a new response from the secondary query answering facility; and providing an audio output based at least in part on the new response from the secondary query answering facility.

16. The apparatus of claim 15, wherein the new response is generated at the secondary query answering facility in a text format and the audio output is created from the new response using a text-to-speech process.

17. The apparatus of claim 15, wherein the operations further comprise:

transmitting the new response to the medical database; and storing the new response in the medical database together with metadata relating to the query.

18. A system for providing medical information, the system comprising:

a speaker;

a microphone;

a medical database; and a processor arrangement programmed to cause the system to perform operations comprising:

converting detected audio signals into a natural language data stream, determining from the natural language data stream whether a voice command for information relating to a medical device or a medicament has been issued by a user, in response to a positive determination, converting at least part of the natural language data stream into a query for querying the medical database, supplying the query to the medical database and receiving a response therefrom, generating an audio output based at least in part on the response from the medical database, determining a user identity of the user, retrieving user data from a user database using the user identity, modifying the audio output based at least in part on the user data, providing the audio output, creating a log of the query, the log comprising the user identity, an identifier of the query, and an identifier of the response provided, and storing the log in the medical database.

* * * * *

UNITED STATES PATENT AND TRADEMARK OFFICE
CERTIFICATE OF CORRECTION

| | | |
|---|---|---|
| PATENT NO. | : 11,581,095 B2 | Page 1 of 1 |
| APPLICATION NO. | : 16/651437 | |
| DATED | : February 14, 2023 | |
| INVENTOR(S) | : Helmer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this
Eleventh Day of February, 2025

Coke Morgan Stewart
*Acting Director of the United States Patent and Trademark Office*